United States Patent
Sakai et al.

(10) Patent No.: US 8,737,718 B2
(45) Date of Patent: May 27, 2014

(54) APPARATUS AND METHOD FOR INSPECTING DEFECT

(75) Inventors: Kaoru Sakai, Yokohama (JP); Takahiro Urano, Ebina (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 13/378,427

(22) PCT Filed: Jun. 18, 2010

(86) PCT No.: PCT/JP2010/004073
§ 371 (c)(1),
(2), (4) Date: Jan. 20, 2012

(87) PCT Pub. No.: WO2011/024362
PCT Pub. Date: Mar. 3, 2011

(65) Prior Publication Data
US 2012/0141012 A1    Jun. 7, 2012

(30) Foreign Application Priority Data
Aug. 26, 2009   (JP) ................. 2009-194960

(51) Int. Cl.
*G06K 9/62*  (2006.01)

(52) U.S. Cl.
USPC .......................................... 382/149

(58) Field of Classification Search
None
See application file for complete search history.

(56) References Cited

U.S. PATENT DOCUMENTS

| | | | |
|---|---|---|---|
| 7,221,992 B2 | 5/2007 | Smith et al. | |
| 8,131,058 B2 | 3/2012 | Shimura | |
| 2007/0019858 A1* | 1/2007 | Shimura | 382/149 |
| 2008/0285023 A1 | 11/2008 | Tsai et al. | |
| 2008/0292176 A1* | 11/2008 | Sakai et al. | 382/144 |
| 2008/0297783 A1* | 12/2008 | Urano et al. | 356/237.5 |
| 2009/0009753 A1* | 1/2009 | Horai et al. | 356/237.3 |

FOREIGN PATENT DOCUMENTS

| | | |
|---|---|---|
| JP | 5-264467 | 10/1993 |
| JP | 2006-300892 | 11/2006 |
| JP | 2007-33073 | 2/2007 |
| JP | 2008-268141 | 11/2008 |
| JP | 2009-14510 | 1/2009 |

* cited by examiner

*Primary Examiner* — Stephen R Koziol
*Assistant Examiner* — Delomia Gilliard
(74) *Attorney, Agent, or Firm* — Antonelli, Terry, Stout & Kraus, LLP.

(57) ABSTRACT

A defect inspection apparatus includes an illumination optical system which irradiates an inspection subject under a predetermined optical condition, a detection optical system which obtains image data by detecting a scattered light from the inspection subject irradiated by the illumination optical system, and an image processing unit provided with a defect candidate detection unit which detects defect candidates with respect to plural image data obtained by the detection optical system under different conditions, and a post-inspection processing unit which executes a defect determination by integrating the defect candidates with respect to the plural image data.

8 Claims, 15 Drawing Sheets

APPARATUS AND METHOD FOR INSPECTING DEFECT

BACKGROUND ART

The present invention relates to an apparatus and a method for inspecting defects for the purpose of detecting a small pattern defect and foreign substance of an inspection subject.

On the manufacturing line of semiconductor substrates or the thin film substrates, the inspection with respect to defects on the surface of the semiconductor substrate or the thin film substrate has been conducted so as to maintain and improve yield of the product.

Patent Literature 1 (Japanese Patent Laid-Open No. 05-264467) discloses "a defect inspection apparatus for inspecting the defect of repeated pattern through the process of comparing a first multiple-value digital signal obtained by delaying the multiple-value digital signal by an amount corresponding to the pitch of the repeated pattern, and a simultaneously converted second multiple-value digital signal, detecting a spatially corresponding positional deviation of the digital signals between the first and the second multiple-values, and adjusting an amount of delay performed by a delay unit so that the positional deviation is optimized" as the related art technique for carrying out the defect detection through comparison between the detected image and the reference image. Patent Literatures 2 (U.S. Pat. No. 7,221,992) and 3 (US 2008/0285023) disclose the method "for discrimination between the defect and noise through the process of simultaneously detecting images under plural different optical conditions, making a comparison with respect to luminance between the image and the reference image, and integrating the resultant comparative values".

CITATION LIST

Patent Literature

Patent Literature 1: Japanese Patent Laid-Open No. Hei 05-264467
Patent Literature 2: US Patent No. 7,221,992
Patent Literature 3: US Publication No. 2008/0285023

SUMMARY OF INVENTION

Technical Problem

According to the related art, when integrating the images simultaneously detected under the different optical conditions, the optical conditions for the images to be integrated are restricted depending on the apparatus configuration. When the images under the different optical conditions detected on time-series basis are detected and integrated to determine the defect, the high-capacity memory and data storage medium for storing those images under the respective optical conditions are indispensable. When picking up the images of the inspection subject under the respective optical conditions on time-series basis through stage scanning, the positional deviation is observed among the images under different optical conditions because of operation error on the stage. Therefore, the position between the respective images has to be corrected for integration. Different optical condition may cause the pattern of the inspection subject to appear different to the greater degree. It is therefore difficult to calculate the positional correction amount.

For the semiconductor wafer as the inspection subject, there may have a very small difference in the film thickness of the pattern between adjacent chips owing to planarization through CMP, thus causing local difference in luminance of the image between chips, as well as difference in luminance between the chips owing to variation in the pattern thickness. When comparing the images of the reference chip with respect to luminance likewise the related art, and the portion at which the comparison result is equal to or larger than the specific threshold value th is identified as the defect, regions with different luminance between the comparative images owing to the difference in the film thickness or variation in the pattern thickness as described above may be detected as the defect. Actually, such region that should not be detected as the defect will become so called false information. As one of the methods for avoiding the false information, the threshold value th for detecting the defect has been conventionally made large. This process, however, reduces sensitivity, failing to detect the defect corresponding to the difference value equal to or lower than the similar level. Meanwhile, there are many kinds of defects, which are classified into the defect that is not required to be detected (hereinafter referred to as "Nuisance defect"), and the defect that is required to be detected. The present invention easily allows detection of various types of defects with high sensitivity, and suppression of increase in noise and Nuisance defects accompanied with the detection with high sensitivity.

Solution to Problem

Representative examples of the present invention disclosed herein will be outlined as below.

(1) A defect inspection apparatus includes an illumination optical system which irradiates an inspection subject under a predetermined optical condition, a detection optical system which detects a scattered light from the inspection subject irradiated by the illumination optical system under a predetermined detection condition, and obtains image data, and an image processing unit which includes a defect candidate detection unit which detects defect candidates with respect to plural image data obtained by the detection optical system under different conditions, respectively, and a post-inspection processing unit which executes a defect determination by integrating the defect candidates with respect to the plural image data.

(2) The post-inspection processing unit of the defect inspection apparatus according to (1) executes the defect determination by integrating the defect candidates through checking of coordinates of the defect candidates with respect to the plural image data.

Advantageous Effects of Invention

The present invention easily allows detection of various types of defects with high sensitivity and suppression of noise and Nuisance defect which increase accompanied with the detection with high sensitivity.

These and other objects, features and advantages of the invention will be apparent from the following more particular description of preferred embodiments of the invention, as illustrated in the accompanying drawings.

DESCRIPTION OF EMBODIMENTS

Exemplary defect inspection apparatus and defect inspection method as embodiments according to the present invention will be described referring to FIGS. 1 to 12. An embodiment of the defect inspection apparatus configured to inspect the semiconductor wafer as the inspection subject under darkfield illumination will be described.

Figure 2:
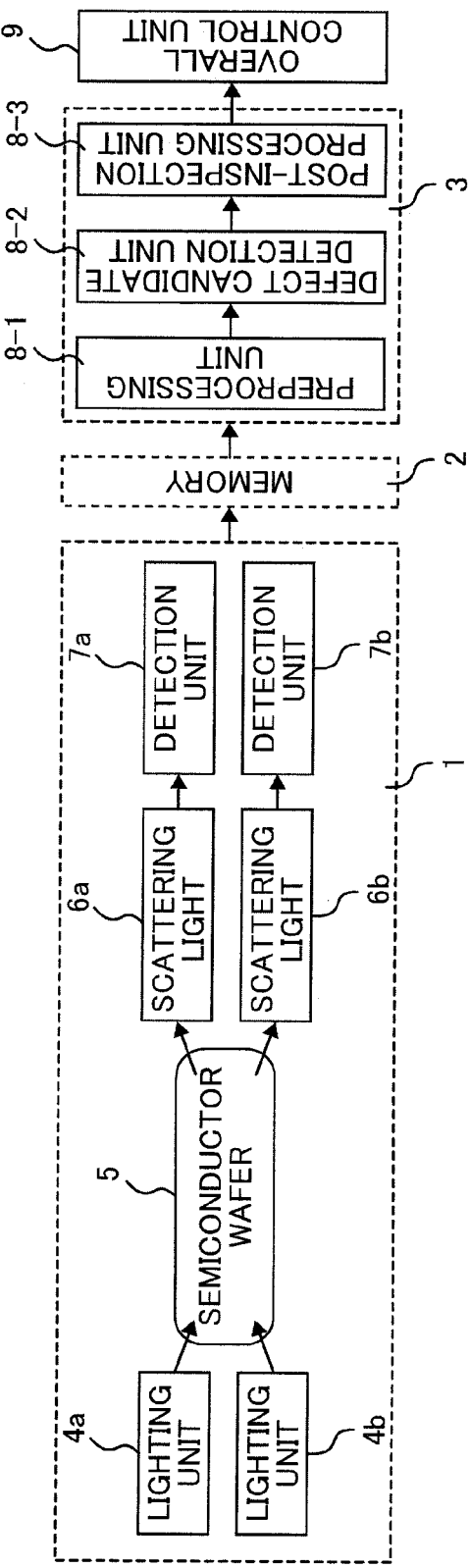
FIG. 2 is an exemplary conceptual view that represents an embodiment of a defect inspection apparatus according to the present invention.

FIG. 2 is a conceptual view illustrating the embodiment of the defect inspection apparatus according to the present invention. The defect inspection apparatus shown in FIG. 2 includes an optical unit 1, a memory 2, an image processing unit 3, and an overall control unit 9.

[Optical Unit 1]

The optical unit 1 is formed of plural lighting units 4a, 4b, and plural detection units 7a, 7b.

The lighting units 4a, 4b irradiate a semiconductor wafer 5 as the inspection subject with lights under different illumination conditions. The illumination condition includes an irradiation angle, an illumination orientation, an illumination wavelength, a polarization state and the like. The illumination lights from the lighting units 4a, 4b allow the inspection subject 5 to generate scattering lights 6a, 6b, respectively, which will be detected as scattering light intensity signals by the detection units 7a, 7b.

[Memory 2]

The memory 2 stores the respective scattering light intensity signals detected by the detection units 7a, 7b of the optical unit 1.

[Image Processing Unit 3]

The image processing unit 3 includes a preprocessing unit 8-1, a defect candidate detection unit 8-2, and a post-inspection processing unit 8-3.

The preprocessing unit 8-1 executes signal correction and image division, which will be described later. The defect candidate detection unit 8-2 subjects the image generated by the preprocessing unit 8-1 to the process to be described later, and detects defect candidates. The post-inspection processing unit 8-3 excludes noise and Nuisance defect (defect type regarded as unnecessary to detect by the user, and the nonfatal defect) from the defect candidates detected by the defect candidate detection unit 8-2 so as to subject the remaining defects to classification and dimension estimation in accordance with the defect type.

In the image processing unit 3, the scattering light intensity signals, input and stored in the memory 2 are subjected to the aforementioned processes in the preprocessing unit 8-1, the defect candidate detection unit 8-2, and the post-inspection processing unit 8-3, which then will be output to the overall control unit 9.

FIG. 2 shows the embodiment in which the scattering lights 6a, 6b are detected by the detection units 7a, 7b, individually. However, they may be commonly detected by the single detection unit. Each number of the lighting units and the detection units does not have to be limited to two, but may be set to one, three or more.

The scattering lights 6a and 6b indicate scattering light distributions which are generated corresponding to the respective lighting units 4a and 4b. If the optical condition of the illumination light of the lighting unit 4a is different from that of the illumination light of the lighting unit 4b, the resultant scattering lights 6a and 6b generated under those conditions become different from each other. According to the present invention, the optical property and features of the scattering light generated by the certain illumination light will be designated as the scattering light distribution of the generated scattering light. More specifically, the scattering light distribution indicates the distribution of the optical parameter value such as intensity, amplitude, phase, polarization, wavelength, coherence and the like corresponding to the emission position, emission orientation and emission angle of the scattering light.

Figure 3:
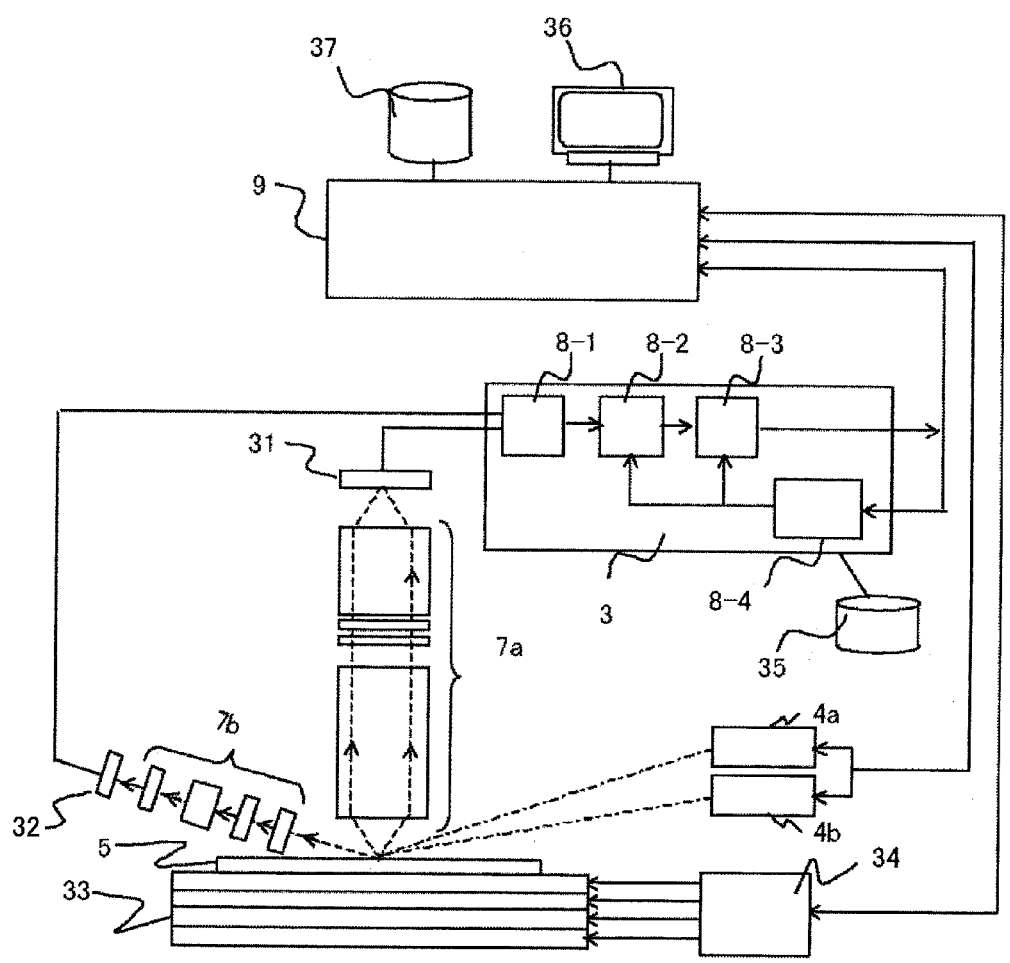
FIG. 3 is an exemplary block diagram of the embodiment of the defect inspection apparatus according to the present invention.

FIG. 3 shows an embodiment of the defect inspection apparatus intended to realize the structure as shown in FIG. 2. The defect inspection apparatus according to the present invention includes a stage 33 which holds the inspection subject (semiconductor wafer 5), plural lighting units 4a, 4b which obliquely radiate illumination lights to the semiconductor wafer 5, a detection optical system (upward detection system) 7a which brings the vertical scattering light from the semiconductor wafer 5 into an image, a detection optical system (oblique detection system) 7b which brings the obliquely directed scattering light into an image, sensor units 31, 32 which receive the optical images formed by the respective detection optical systems, and convert the images into image signals, the memory 2 which stores the obtained image signals, the image processing unit 3 which processes the images based on the scattering light intensity signals input from the memory 2, the overall control unit 9, and a mechanical controller 34 which moves the stage under the control of the overall control unit 9.

The semiconductor wafer 5 is supported on the stage (X-Y-Z-θ stage) 33, and is movable and rotatable in XY plane, and movable toward Z direction. The X-Y-Z-θ stage 33 is driven by the mechanical controller 34. The semiconductor wafer 5 is mounted on the X-Y-Z-θ stage 33 while being horizontally moved so that the scattering light from the foreign substance on the inspection subject is detected. This makes it possible to obtain the detection result as the two-dimensional image.

The lighting units 4a, 4b obliquely irradiate the semiconductor wafer 5 with illumination light rays. Arbitrary illumination light source, for example, laser and lamp may be employed. The light from the respective illumination light sources may have short wavelength or wavelength in broad spectrum (white light). The light with wavelength in ultraviolet region (ultraviolet light: UV light) may be employed as the light with short wavelength for the purpose of enhancing resolution of the image to be detected (detecting very small defect). When using the laser with single wavelength as the light source, it is possible to provide the lighting units 4a, 4b with units (not shown) for reducing coherence property, respectively.

The detection optical systems 7a, 7b detect scattering lights each having the optical path branched from the semiconductor wafer 5. The detection optical system (upward detection system) 7a is the detection optical system which brings the vertical scattering light into the image on the surface of the semiconductor wafer 5. The detection optical system (oblique detection system) 7b is the detection optical system which brings the oblique scattering light into the image on the surface of the semiconductor wafer 5.

The sensor units 31, 32 receive and convert the optical images formed by the respective detection optical systems 7a, 7b into image signals, respectively. When using an image sensor of time delay integration type (Time Delay Integration Image Sensor: TDI image sensor) formed by two-dimensionally arranging plural one-dimensional image sensors, the signal detected by each of the one-dimensional image sensors in synchronization with movement of the X-Y-Z-θ stage 33 is transferred and added to the one-dimensional image sensor in the subsequent stage. This makes it possible to provide the two-dimensional image with high sensitivity at relatively high speed. The sensor of parallel output type with plural output taps is used as the TDI image sensor so that outputs from the sensor are processed in parallel, thus ensuring higher speed detection.

The image processing unit 3 includes the preprocessing unit 8-1, the defect candidate detection unit 8-2, the post-inspection processing unit 8-3, and a parameter setting unit 8-4. The image processing unit 3 extracts the defect on the semiconductor wafer 5 as the inspection subject based on the scattering light intensity signals input from the memory 2.

Specifically, the preprocessing unit 8-1 subjects the image signals input from the sensor units 31, 32 to such image correction as shading correction and dark level correction so that the image is divided into those with sizes each in constant unit. The defect candidate detection unit 8-2 detects the defect candidate from the images which have been corrected and divided. The post-inspection processing unit 8-3 excludes Nuisance defect and noise from the detected defect candidates, and subjects the remaining defects to classification in accordance with the defect type and dimension estimation. The parameter setting unit 8-4 receives externally input parameters and set the input parameters in the defect candidate detection unit 8-2 and the post-inspection processing unit 8-3. The parameter setting unit 8-4 is formed by connecting the image processing unit 3 to a database 35, for example.

The overall control unit 9 provided with a CPU (built in the overall control unit 9) for executing various control processes is appropriately connected to a user interface unit (GUI unit) 36 and a data storage unit 37.

The user interface unit (GUI unit) 36 includes a display unit and an input unit for receiving parameters from the user and displaying images of the detected defect candidate, and finally extracted defect. The data storage unit 37 stores feature quantities and images of the defect candidates detected by the image processing unit 3.

The mechanical controller 34 drives the X-Y-Z-θ stage 33 based on the control instruction from the overall control unit 9. The image processing unit 3, and the detection optical systems 7a, 7b are also driven upon instruction from the overall control unit 9.

The semiconductor wafer 5 as the inspection subject has a large number of regularly arranged chips with the same patterns each having the memory mat portion and a peripheral circuit portion. The overall control unit 9 continuously moves the semiconductor wafer 5 by controlling the X-Y-Z-θ stage 33, and simultaneously allows the sensor units 31, 32 to take images of the chips sequentially. Then comparison is made between the obtained two kinds of scattering lights (6a, 6b) and the corresponding images at the same positions of the regularly arranged chips so as to extract the defect. The flow of the inspection as described above will be explained referring to FIG. 4.

Figure 4:
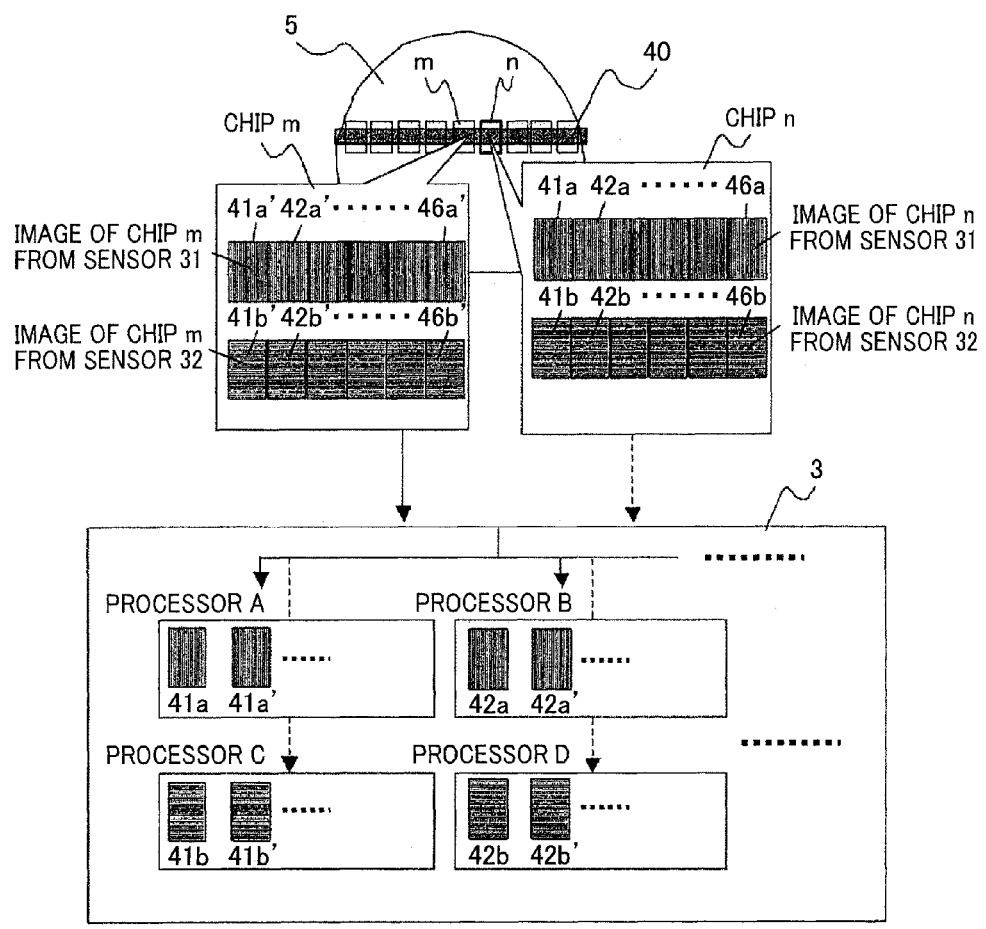
FIG. 4 is an explanatory view representing a relationship between the sensor and the chip to be detected.

It is assumed that an image of a belt-like region 40 of the semiconductor wafer 5 is obtained as a result of scanning on the X-Y-Z-θ stage 33, and the chip n is used as the one to be inspected. Then divided images 41a, 42a, . . . , 46a are obtained by dividing the image of the chip n derived from the sensor unit 31 into 6 parts. Divided images 41a', 42a', . . . , 46a' are obtained by dividing the image of the adjacent chip m into 6 parts likewise the chip n. Those divided images derived from the same sensor unit 31 are vertically striped. Meanwhile, divided images 41b, 42b, . . . , 46b of the chip n, and divided images 41b', 42b', . . . , 46b' of the adjacent chip m are derived from the sensor unit 32. Those divided images derived from the same sensor unit 32 are horizontally striped. According to the present invention, each image of two different detection systems input into the image processing unit 3 is divided so that the divided positions correspond with each other between the chips. The image processing unit 3 is formed of plural processors operated in parallel. The corresponding images (for example, divided images 41a and 41a' at positions corresponding to the chips n and m, which are derived from the sensor unit 31, and divided images 41b and 41b' at positions corresponding to the chips n and m, which are derived from the sensor unit 32) are input into the same processor. The respective processors execute the defect candidate detection in parallel from the positions corresponding to the respective chips, which have been input from the same sensor unit. In the case where images of the same region, each having different combination of the optical and detection conditions are input simultaneously, plural processors detect the defect candidates in parallel (for example, processors A and C, and processors B and D as shown in FIG. 4 execute the detection in parallel, respectively). Meanwhile, it is possible to detect the defect candidates on the time-series basis from the images each having the different combination of optical and detection conditions. For example, the defect candidate may be detected from the divided images 41b and 41b' by the processor A subsequent to the process performed by the same processor A for detecting the defect candidate from the divided images 41a and 41a'. The correlation between the processors and the divided images may be arbitrarily set so long as the divided images at the positions corresponding to the chips are input to the same processor with respect to the images under plural optical conditions, and the defect candidate is detected for each image under the respective optical conditions.

Figure 5:
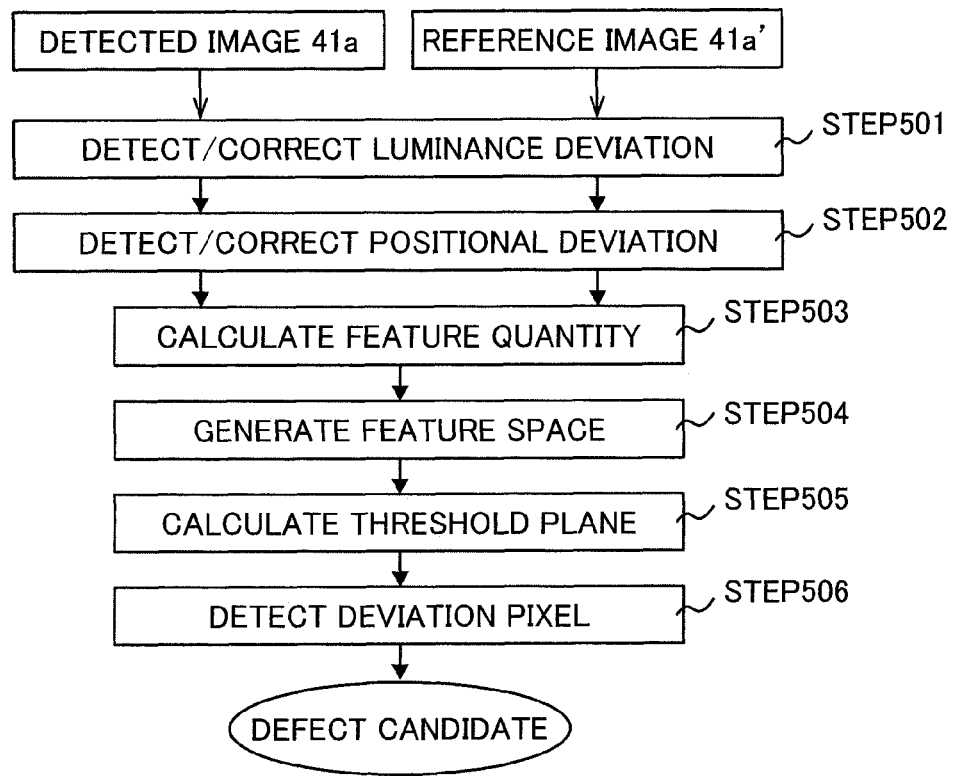
FIG. 5 shows an example of an explanatory view of the process flow executed by the defect candidate detection unit according to the present invention.

FIG. 5 represents the flow of the process for detecting the defect candidates based on the divided images (41a; 41a') derived from the sensor unit 31, which is performed by the defect candidate detection unit 8-2 of the image processing unit 3.

It is assumed that the processor A executes the process using the divided image 41a at the head of the chip n derived from the sensor unit 31 as the inspection subject image (hereinafter referred to as "detected image") and the divided image 41a' of the region corresponding to the adjacent chip m as the reference image.

The defect candidate detection unit 8-2 makes a comparison between the detected image 41a and the reference image 41a' so that luminance deviation is detected and corrected (step 501). Then the positional deviation is detected and corrected (step 502), and feature quantity defined by the pixel corresponding to the detected image 41a and the pixel corresponding to the reference image 41a' is calculated (step 503). Thereafter, feature space is generated based on the arbitrary feature quantity of the subject pixel (step 504). The threshold plane is calculated in the feature space (step 505), and the defect candidate is detected based on deviation of the pixel from the threshold plane (step 506).

The semiconductor wafer 5 has the same patterns regularly arranged as described above. So the detected image 41a and the reference image 41a' should be the same under normal conditions. However, the wafer 5 formed of a multi-layer film may cause large luminance deviation among the images owing to difference in the film thickness among the chips. The position at which the image is obtained tends to deviate among the chips owing to vibration during scanning by the stage. So the luminance deviation has to be corrected by the defect candidate detection unit 8-2. According to the embodiment, such process is executed in an initial stage by the defect candidate detection unit 8-2. However, detection and correction of the luminance deviation may be executed by the portion other than the defect candidate detection unit 8-2.

Figure 6:
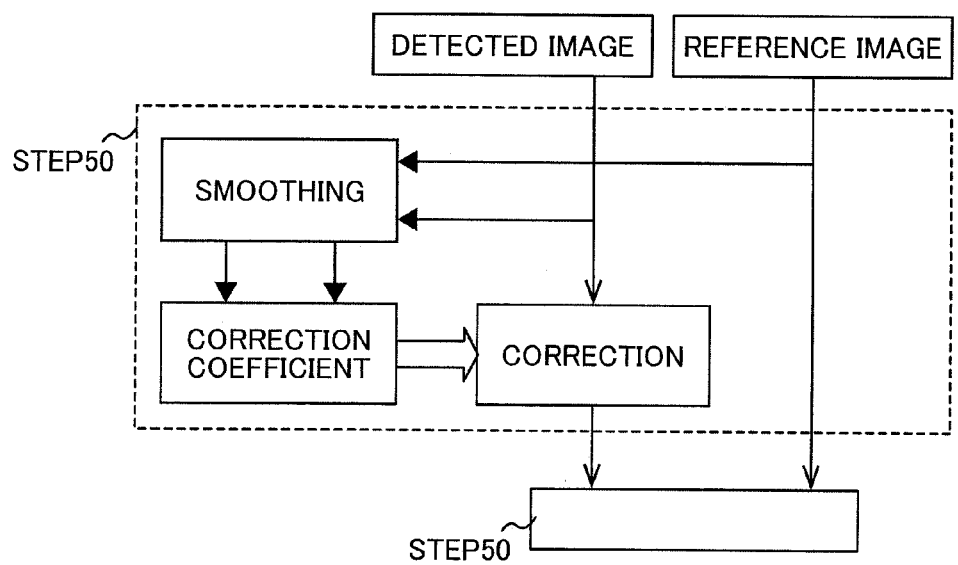
FIG. 6 is an explanatory view of the process flow of luminance deviation detection/correction step executed by the defect candidate detection unit according to the present invention.

FIG. 6 represents the process flow of luminance deviation detection/correction step (step 501).

In step 501, a smoothing filter shown by (formula 1) is applied to the detected image 41a, and the reference image 41a' which are input. The (formula 1) is an example of smoothing by applying two dimensional Gauss function of average 0, distribution $\sigma^2$ to each pixel value f(x,y) of the images 41a and 41a'. However, smoothing may be performed through simple averaging as represented by (formula 2), or use of the median filter which takes the median value in the local region. Then the correction coefficient is calculated for correcting the luminance deviation between the images. The least squares approximation using all the pixels in the image is described as the example. Specifically, it is assumed that a linear correlation is established as represented by (formula 3) between the respective pixel values Gf(x,y) and Gg(x,y) of the smoothed images 51a and 51a'. The values a and b are calculated so that (formula 4) is minimized. The obtained values are set as the correction coefficients gain and offset. All the pixel values f(x,y) of the detected image before smoothing are subjected to the luminance correction as indicated by (formula 5).

$$G(x,y)=(1/2\,\pi\sigma^2)\cdot\exp(-(x^2+y^2)/2\sigma^2)$$

$$G(f(x,y))=G(xy)*f(x,y) \quad\quad\quad \text{(Formula 1)}$$

where * denotes convolution.

$$G(f(x,y))=\frac{1}{m\cdot n}\sum_{k=1}^{m}\sum_{l=1}^{n}f(x-[(m-1)/2]+k-1,y-[(n-1)/2]+l-1) \quad\quad \text{(Formula 2)}$$

where m,n denote matrix sizes for smoothing, and [ ]denotes Gaussian code.

$$G(g(x,y))=a+b\cdot G(f(x,y)) \quad\quad\quad \text{(Formula 3)}$$

$$\Sigma\{G(g(x,y))-(a+b\cdot G(f(x,y)))\}^2 \quad\quad\quad \text{(Formula 4)}$$

$$L(f(x,y))=\text{gain}\cdot f(x,y)+\text{offset} \quad\quad\quad \text{(Formula 5)}$$

In positional deviation (or shift) detection/correction step (step 502), generally the deviation (or shift) amount which minimizes the square sum of the brightness difference between images is obtained while displacing one of the images. Alternatively, with the general method, the deviation amount which maximizes the normalized correlation coefficient is obtained while displacing one of the images.

In feature space generation step (step 504), all or arbitrary number of the feature quantities of the subject pixels calculated in step 503 are selected to generate the feature space. Arbitrary feature quantity may be set so long as it represents the feature of the pixel, for example, (1) contrast, (2) shading difference, (3) luminance dispersion value of adjacent pixel, (4) correlation coefficient, (5) luminance change with respect to the adjacent pixel, and (6) quadratic differential. Assuming that the luminance of each point of the detected images is set to f(x,y), and the luminance of the corresponding reference image is set to g(x,y), the aforementioned feature quantity as the embodiment may be calculated from a set of the images (41a and 41a') using the following formula.

$$\text{Contrast: } \max\{f(x,y),f(x+1,y),f(x,y+1),f(x+1,y+1)\}-\min\{f(x,y),f(x+1,y),f(x,y+1),f(x+1,y+1)\} \quad \text{(Formula 6)}$$

$$\text{Shading difference: } f(x,y)-g(x,y) \quad\quad\quad \text{(Formula 7)}$$

$$\text{Dispersion: } [\Sigma(f(x+i,y+j)^2)-\{\Sigma f(x+i,y+j)\}^2/M]/(M-1) \quad \text{(Formula 8)}$$

where i,j=-1, 0, 1
M=9

Furthermore, luminance of each of those images (detected image 41a, reference image 41a') is set as the feature quantity as well. For the feature quantity of the embodiment, two luminance values f(x,y) and g(x,y) of the detected image 41a and the reference image 41a' respectively are selected. The feature space is generated by plotting values of all the pixels in the two-dimensional space while setting X and Y values at f(x,y) and g(x,y), respectively.

In the threshold plane calculation step (step 505), the threshold plane is calculated within the feature space (two-dimensional space in this embodiment) generated in step 504 as the feature space generation step.

In the deviation pixel detection step (step 506), the defect candidate is detected based on the threshold plane, for example, the pixel outside the threshold plane, that is, the pixel characteristically set as the deviation value is detected as the defect candidate.

The embodiment having the two-dimensional feature space in step 504 has been described. However, multidimensional feature space may be employed while setting some of or all the plural feature quantities as axes.

Figure 7:
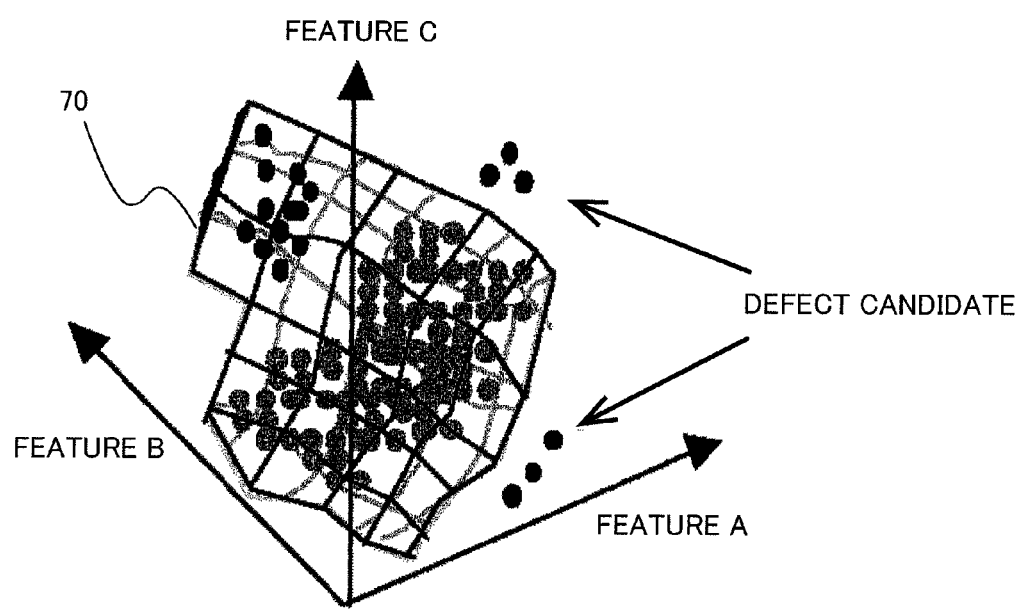
FIG. 7 shows an example of the feature space generated by the defect candidate detection process according to the present invention.

FIG. 7 shows an embodiment of the two-dimensional feature space defined by three feature quantities. Respective pixels of the subject image are plotted in the feature space having the feature quantities A,B,C set as axes in accordance with each value of the features A,B, and C. Then the threshold plane is set so that the distribution estimated as normal is surrounded. Referring to the drawing, a polygonal plane 70 represents the threshold plane, pixels surrounded by the plane 70 are determined as normal (including noise), and deviated pixels outside the plane are determined as defect candidates. The normal range may be estimated by the user through the method for setting the threshold value individually. Alternatively, the normal range may be identified in accordance with likelihood that the subject pixel is the non-defect pixel while assuming that the distribution of the feature of the normal pixel follows the normal distribution. According to the latter method, assuming that the d feature quantities of n normal pixels are designated as x1, x2, . . . , xn, a discriminant function Φ for detecting the pixel that sets the feature quantity to x as the defect candidate may be obtained by calculating the following formulae (Formula 9) and (Formula 10).

$$p(x) = \frac{1}{(2\pi)^{\frac{d}{2}} \sqrt{|\Sigma|}} \exp\left\{-\frac{1}{2}(x-\mu)^t \sum\nolimits^{-1} (x-\mu)\right\} \quad \text{(formula 9)}$$

where μ denotes average of all the pixels $$\mu = \frac{1}{n}\sum_{i=1}^{n} x_i,$$

and Σ denotes covariance $$\Sigma = \Sigma_{i=1}^{n}(x_i-\mu)(x_i-\mu)^t \quad \text{(Formula 10)}$$

Discriminant function
Φ(x)=1 (if p(x)≥th then non-defective
Φ(x)=0 (if p(x)<th then defective)

The defect candidate detection unit 8-2 subjects the respective images of the semiconductor wafer 5 in the inspection subject region, which are input from the sensor units 31, 32 to the aforementioned process.

Figure 1:
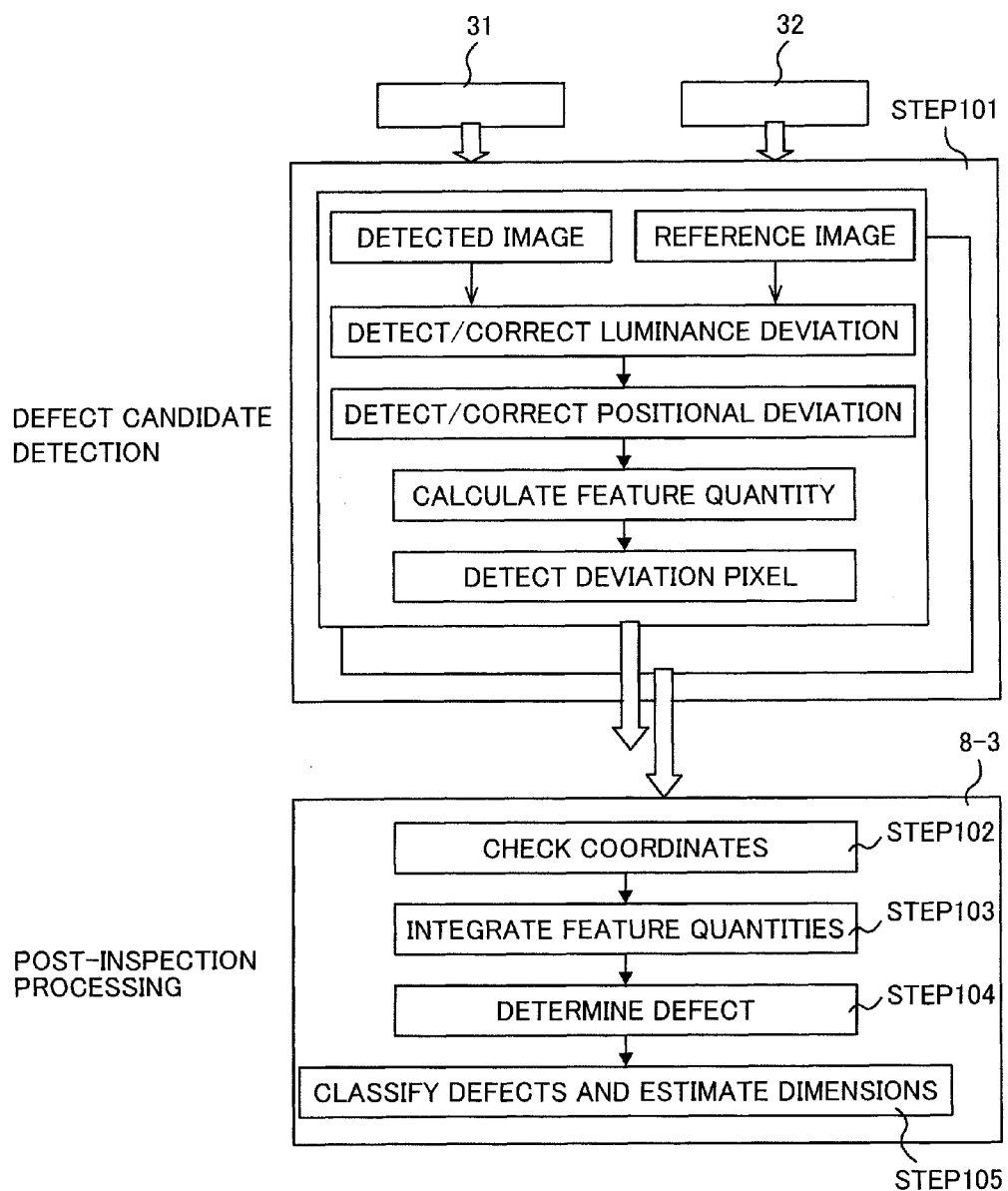
FIG. 1 is an explanatory view with respect to processing flow of defect candidate detection unit and a post-inspection processing unit.
Figure 8:
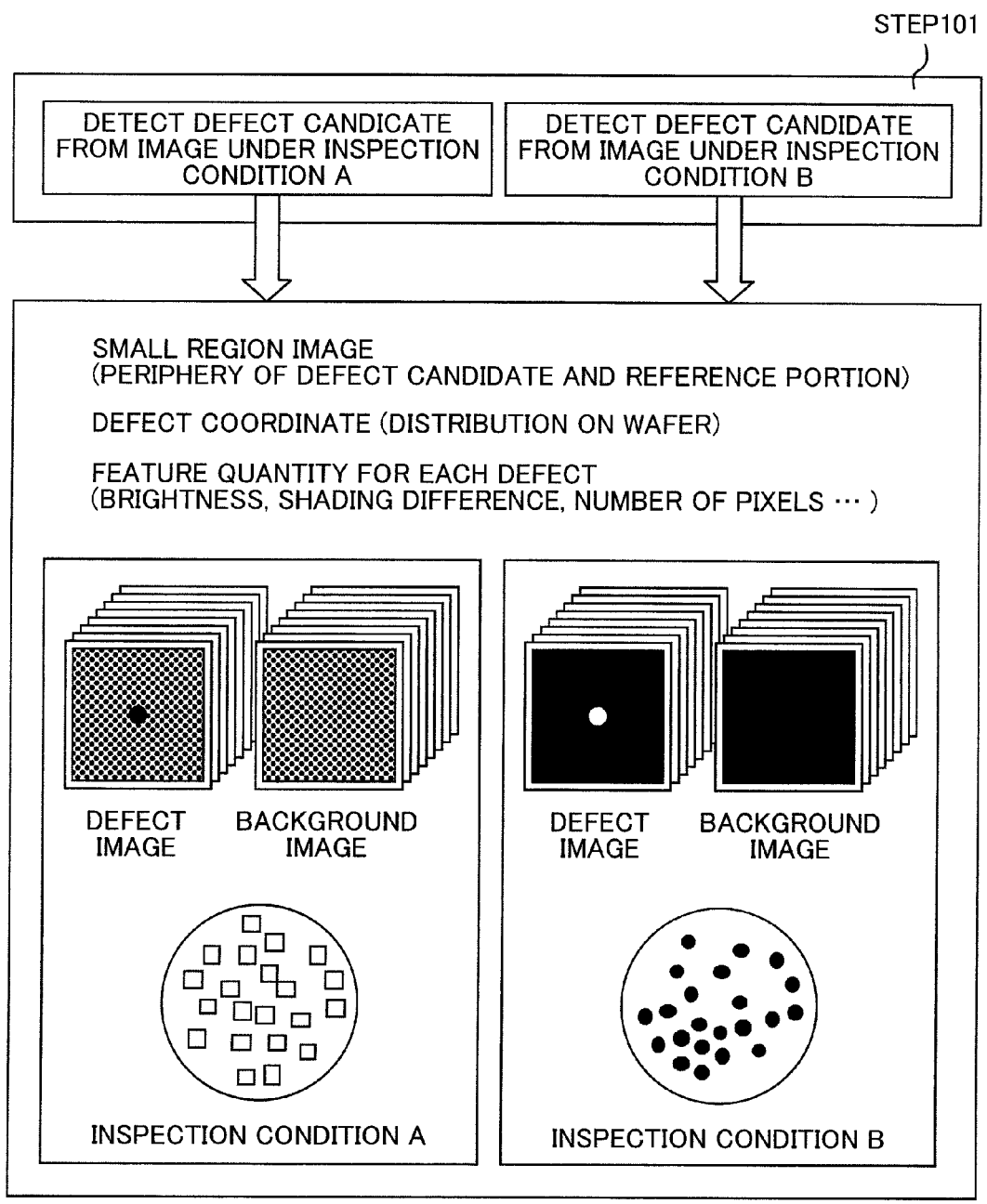
FIG. 8 shows an example of the data detected by the defect candidate detection unit according to the present invention.

FIGS. 1 and 8 represent the process flow in which Nuisance defect and noise are excluded from the defect candidates detected by the defect candidate detection unit 8-2 in the post-inspection processing unit 8-3 of the image processing unit 3, and the remaining defects are classified and estimated with respect to dimension in accordance with the defect type.

FIG. 1 shows an embodiment of the defect detection process (from input to final output of the image), which is executed by the image processing unit 3 according to the present invention.

As described above, the defect candidate detection unit 8-2 detects the defect candidate for each inspection condition based on the images obtained by the sensor units 31, 32 under different combinations (hereinafter referred to as "inspection condition") of the optical and detection conditions which are input (step 101). Then the post-inspection processing unit 8-3 checks the coordinates of the defect candidates on the wafer (step 102), and integrates the feature quantities (step 103). The defect determination with respect to the detected defect candidate is executed, and the true defect is extracted (step 104). The one determined as the true defect is subjected to the defect classification and dimension estimation (step 105).

FIG. 8 shows an example of data relevant to the defect candidates detected by the defect candidate detection unit 8-2 in step 101. Referring to FIG. 8, the defect candidate has features, for example, periphery portion (defect image shown in the drawing), which includes the defect candidate cut from the detected image, the small regional image which includes the background image cut from the reference image at the position corresponding to the defect candidate, the coordinate of the defect candidate on the semiconductor wafer (distribution), the shading difference, the brightness value, and the like.

In the coordinate check step (step 102), with respect to images output from the defect candidate detection unit 8-2 under inspection conditions A and B, respectively, coordinates of the defect candidates on the wafer detected under respective inspection conditions A and B will be checked. In other words, each of the defect candidates is checked whether or not it is detected under both of the conditions A and B.

In the feature quantity integration step (step 103), if the subject defect candidate is the one detected under both the conditions A and B, the respective feature quantities are integrated. For example, the ratio between the brightness value of the defect candidate derived from the condition A and that of the defect candidate derived from the condition B may be used.

In the defect determination step (step 104), it is determined whether the detected defect candidate is noise, Nuisance defect or the true defect so that only the true defect is extracted.

In classification/dimension estimation step (step 105), the extracted defect determined as true is subjected to the defect classification and dimension estimation.

The defect inspection apparatus according to the present invention is configured to individually detect the defect candidate from plural different inspection conditions, and to make a final defect determination by integrating the detection results.

Figure 9A:
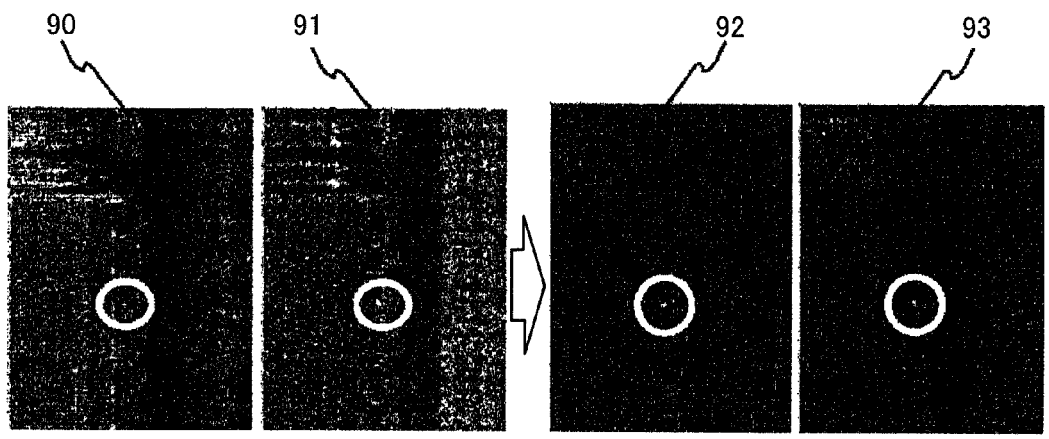
FIG. 9A shows images indicating the difference as a result of the defect inspection using the embodiment according to the present invention.
Figure 9B:
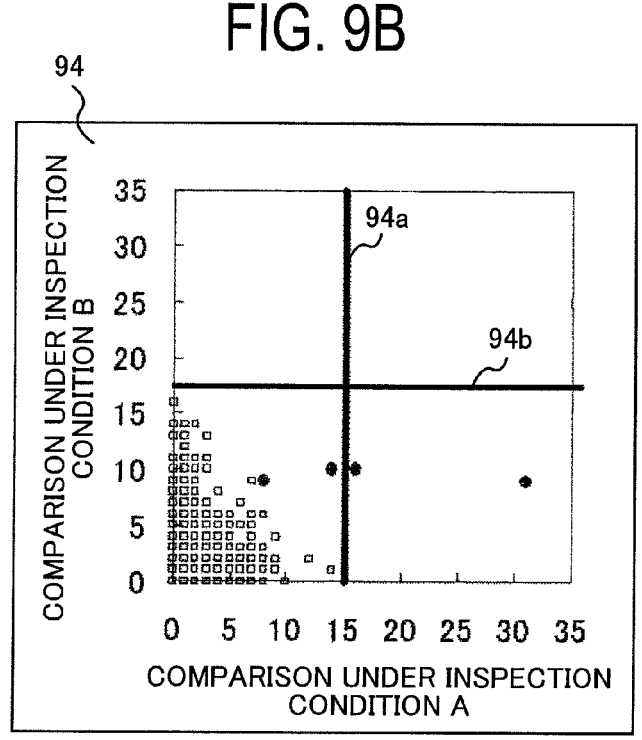
FIG. 9B is an exemplary scatter diagram indicating results of the defect inspection under two different inspection conditions.

FIGS. 9A and 9B show an example as a result of the defect inspection according to the embodiment. Images 90, 91 shown in FIG. 9A represent distribution of the feature quantities in the region which includes the defects when setting the brightness difference between the detected image and the reference image with respect to images detected under two different conditions A and B as the feature quantity, that is, the differential image having the brightness difference expressed in terms of luminance. The brighter the image becomes, the larger the brightness difference is made. The encircled center portion of the image represents the defect. The defect portion has a large brightness difference, and the peripheral region also has the brightness difference that is equal to or larger than that of the defect portion. It is therefore difficult to detect the defect as the deviation value. Meanwhile, images 92, 93 are obtained by subjecting the differential images of those 90, 91 to noise suppression process through whitening. They clearly make the defect portion more obvious.

Figure 9C:
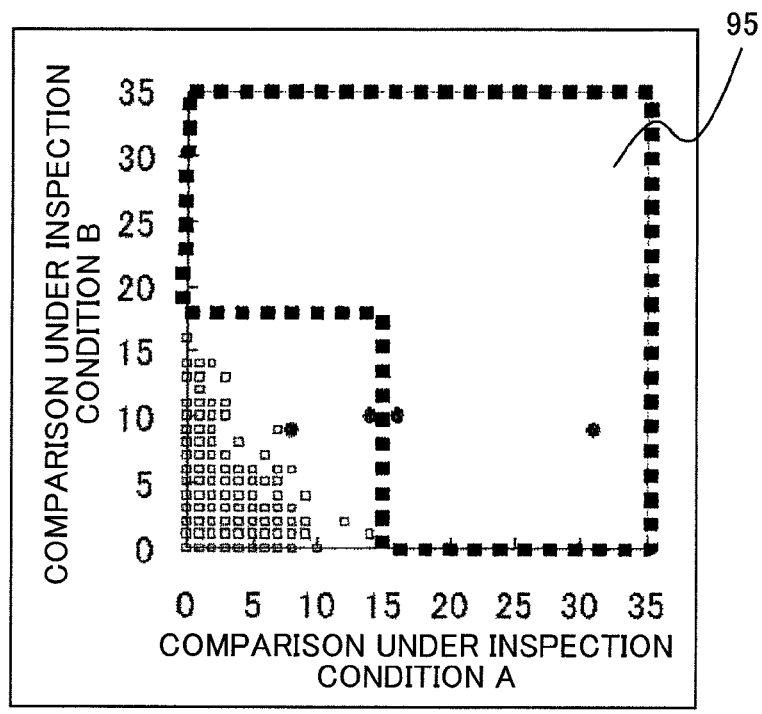
FIG. 9C is an exemplary scatter diagram indicating results of the defect inspection under two different inspection conditions.
Figure 9D:
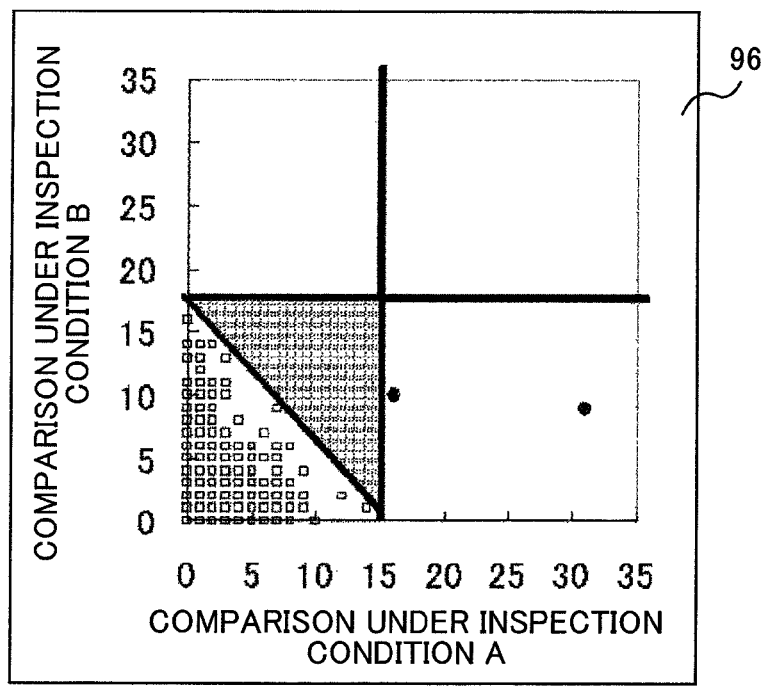
FIG. 9D is an exemplary scatter diagram indicating results of the defect inspection under two different inspection conditions.
Figure 9E:
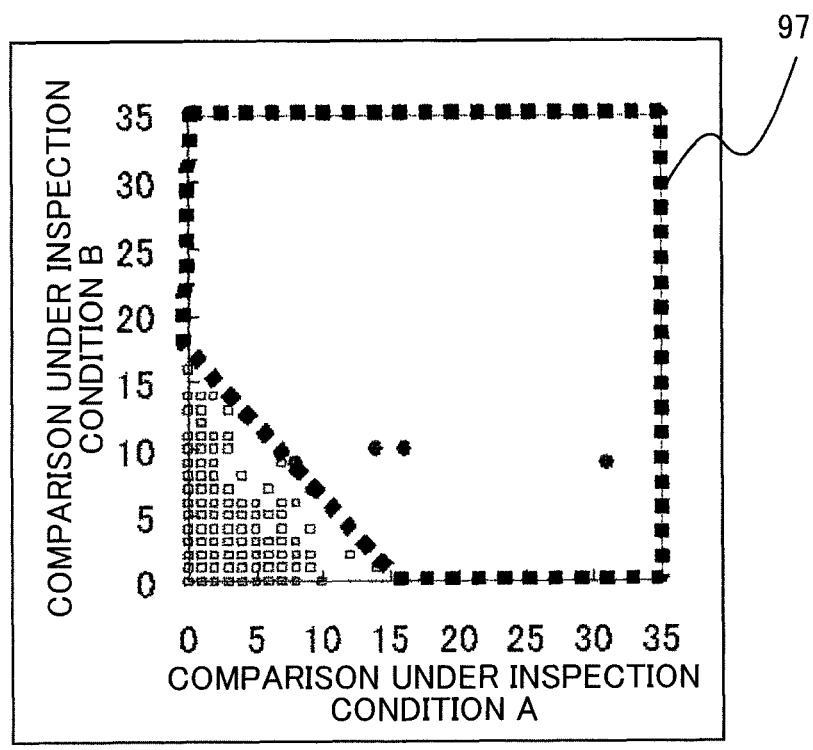
FIG. 9E is an exemplary scatter diagram indicating results of the defect inspection under two different inspection conditions.

A reference numeral 94 shown in FIG. 9B denotes a scatter diagram having values of the image 92 (whitened feature quantities calculated from the images under the inspection condition A) on the X-axis, and values of the image 93 (whitened feature quantities calculated from the images under the inspection condition B) on the Y-axis. In this case, the shading difference is used as the feature quantity. The points plotted with black circles shown in FIG. 9B represent the defect portions, and the remaining portion represents the normal pattern. Reference numerals 94a and 94b in the scatter diagram represent threshold values required to prevent detection of noise (normal pattern) from the respective images under the inspection conditions A and B. That is, the defect may be detected from the image under the inspection condition A in the region with the shading difference larger than that of the threshold value 94a. The defect may be detected from the image under the inspection condition B in the region with the shading difference larger than that of the threshold value 94b. A region 95 surrounded by a dashed line shown in FIG. 9C denotes the region where the defect is detectable under any one of the inspection conditions A and B. Meanwhile, feature quantities calculated from images under the inspection conditions both A and B are integrated to set the threshold value so as to expand the defect detectable region. When estimating the normal range on the two-dimensional scatter diagram, a shaded region 96 shown in FIG. 9D is to be expanded in principle relative to the region 95 shown in FIG. 9C. A region 97 surrounded by the dashed line shown in FIG. 9E is the region where the defect candidate is detectable as the deviation value in the case where the normal range is estimated by integrating the images under two inspection conditions. The drawing clearly shows that the defect pixels plotted with black circles are detectable with higher sensitivity.

Figure 10A:
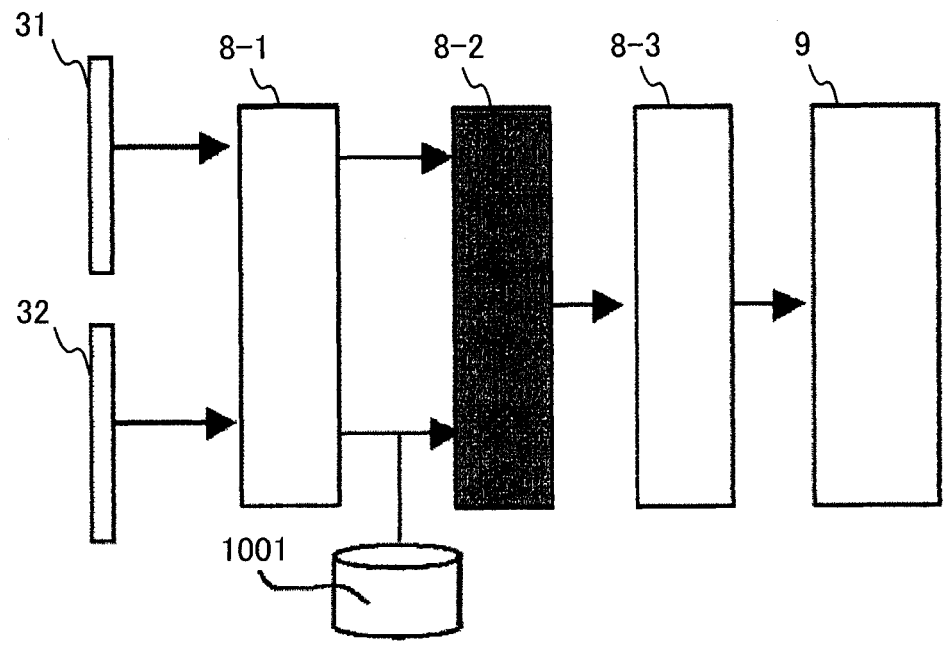
FIG. 10A shows an exemplary system configuration for performing the defect determination by integrating image information data from two different inspection conditions.

FIG. 10A shows an example of a system configuration for defect determination by integrating images obtained under different optical conditions. Images under different inspection conditions from the sensor units 31, 32 are input to the preprocessing unit 8-1, and subjected to the respective processes. They are then input to the defect candidate detection unit 8-2 where the feature quantities are calculated from the respective images, and integrated to detect the defect candidates. The detected defect candidates are classified by the post-inspection processing unit 8-3. When making the defect determination by integrating the images by the defect candidate detection unit 8-2, it is preferable to correlate the images under different inspection conditions at the pixel level. Meanwhile, when images of the inspection subject is picked up while performing the stage scanning, any one of the following procedures is required for integration while correlating the images under the different inspection conditions at the pixel level because of deviation in the image scanning position caused by stage operation error. That is, any one of the procedures of (1) simultaneous scanning and simultaneous pick-up of the images to be integrated and (2) images derived from scanning on time-series basis are integrated after aligning positional deviations has to be performed. When performing (1), the stage operation error and deviation in the image scanning position do not occur. This may enhance detection accuracy, but two or more sensor units are required, thus enlarging the system size. Furthermore, the inspection conditions for images to be integrated are restricted depending on the system configuration. When performing (2), the image under the first inspection condition has to be stored until pick-up of the image under the second inspection condition starts, thus requiring the memory and data storage medium with large capacity as indicated by 1001 in the drawing. The pattern of the subject may appear very different when the inspection condition differs. So this may fail to provide the common pattern for aligning the positional deviation.

Figure 10B:
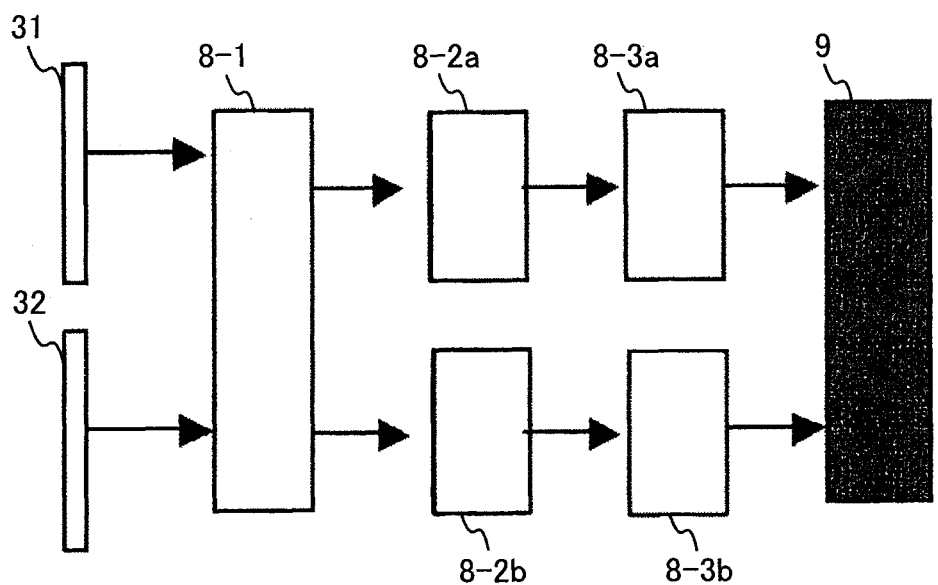
FIG. 10B shows an exemplary system configuration for performing the defect determination by integrating image information data from two different inspection conditions.
Figure 10C:
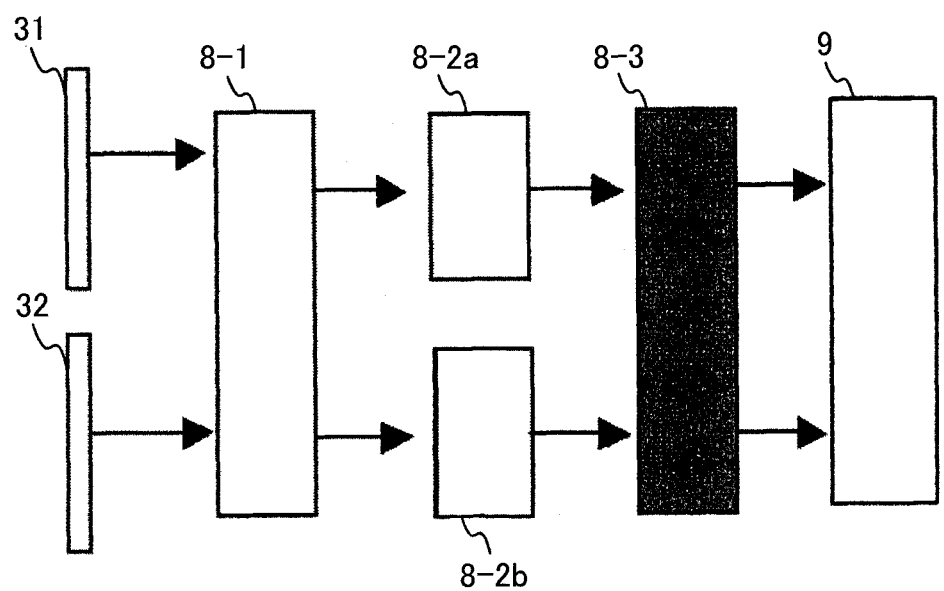
FIG. 10C shows an exemplary system configuration for performing the defect determination by integrating image information data from two different inspection conditions.

FIG. 10B shows an example which integrates results of plural inspection conditions more easily. In this example, two kinds of images are input, and individually subjected to the defect candidate detection processes (8-2a), (8-2b), and post-inspection processes (8-3a), (8-3b) so that the final results are only integrated and displayed by the overall control unit 9. The integration may be made by taking AND/OR of the obtained results. In spite of the simple process, referring to the configuration shown in FIG. 10B, the region 95 illustrated in FIG. 9C is the defect detectable region, and sensitivity becomes lower than that of the configuration shown in FIG. 10A. The integration method according to the present invention is allowed to take the configuration shown in FIG. 10C. In this case, two types of images to be input are individually subjected to the defect candidate detection processes (8-2a), (8-2b), and then the defect determination is made through the post-inspection process (8-3) using the information of the defect candidates detected under the respective conditions.

Figure 11:
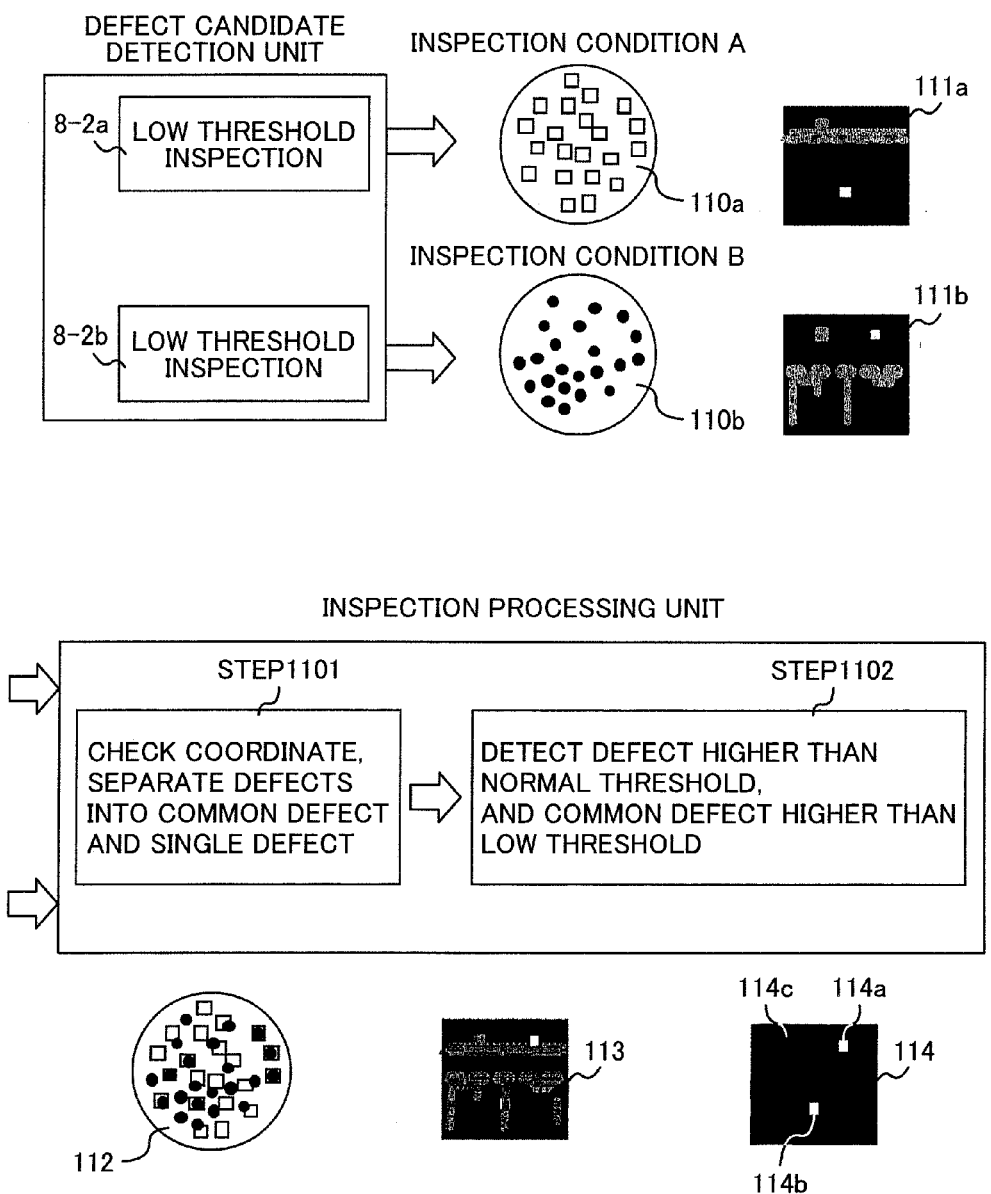
FIG. 11 is an explanatory view of the defect determination process executed by the defect candidate detection unit and the post-inspection processing unit according to the embodiment of the present invention.

FIG. 11 shows an exemplary outline of the defect determination process executed by the post-inspection processing unit (8-3). The processes (8-2a), (8-2b) under the respective inspection conditions, which are executed by the defect candidate detection unit may take the low threshold for the inspection with high sensitivity. In other words, the parameter for each image process is adjusted so as to set the threshold value for determining a defect low. As will be understood, many noises are detected as well as the very small defects. Reference numerals 110a, 110b represent the distribution of the defect candidates individually detected under the respective inspection conditions on the wafer (coordinates of the respective defect candidates on the wafer). Reference numerals 111a, 111b represent the defect candidates detected in the common divided image based on the low threshold value under the inspection conditions A and B, respectively while setting the brightness difference between the detected image and the reference image as the feature quantity. The black region denotes the pixel having the value equal to or lower than the threshold value. The remaining portions denote pixels detected as the defect candidates in excess of the set threshold value. This shows that the higher the luminance, the larger the brightness difference. When results derived from the two different inspection conditions are input to the post-inspection processing unit 8-3, wafer coordinates of the defect candidates detected under the respective conditions is checked, that is, 110a and 110b are superimposed so that the defects are divided into the defect commonly calculated from the defect candidates (hereinafter referred to as "common defect"), and the defect detected from only one of the conditions (hereinafter referred to as "single defect")(step 1101). A reference numeral 112 represents the state where the 110a and 110b are superimposed. It is evaluated whether the coordinates on the wafer are superimposed in the preliminarily set range (unit:nm, pixel) by checking. A reference numeral 113 represents results of superposition of the defect candidates 111a, 111b in the divided image, which are detected under the respective inspection conditions. The defect/noise discrimination which has been made based on results of the superposition between the plural conditions will be described as an example.

The one calculated using the normal threshold values (for example, 94a, 94b shown in FIG. 9B) is determined as the defect. Then the defect candidate with the value equal to or lower than the normal threshold value, but is set as the common defect based on the low threshold value is determined as the defect. The other defect candidates (not calculated based on the normal threshold value, but calculated under only one of the inspection conditions based on the low threshold value) will be excluded as noise (step 1102). A reference numeral 114 represents the result obtained by excluding the noise from the defect candidates in the divided image of 113 based on the aforementioned determination. Reference numerals 114*a*, 114*b* are calculated under any one of the inspection conditions based on the normal threshold value. The reference numeral 114*c* is calculated under both the inspection conditions based on the low threshold value.

Figure 12A:
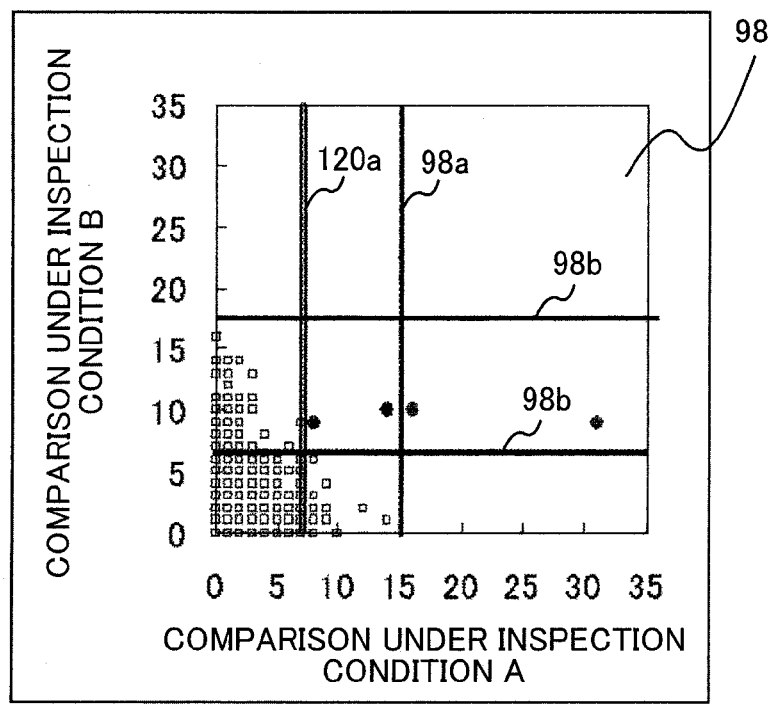
FIG. 12A is an exemplary scatter diagram indicating results of the defect inspection according to the embodiment of the present invention.
Figure 12B:
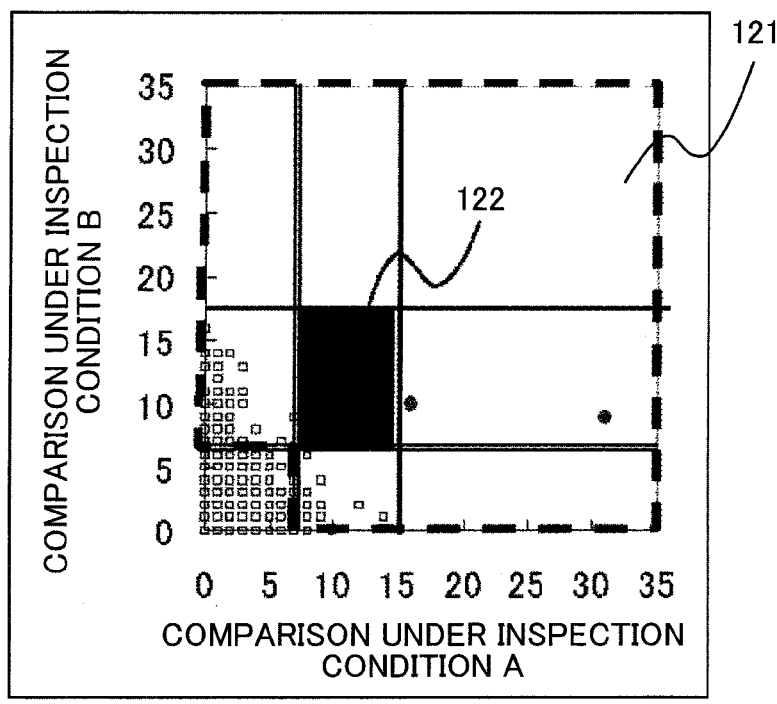
FIG. 12B is an exemplary scatter diagram indicating results of the defect inspection according to the embodiment of the present invention.

An example of results derived from the embodiment of the present invention will be described referring to FIGS. 12A and 12B. FIG. 12A shows 98 as a scatter diagram in which the brightness difference between the detected image and the reference image among those obtained under two different inspection conditions A and B is set as the feature quantity, and whitening process is performed as shown in FIGS. 9A to 9E. Reference numerals 98*a*, 98*b* in the scatter diagram represent threshold values required to prevent detection of noise (normal pattern) from the respective images under the inspection conditions A and B, that is, normal threshold values. Reference numerals 120*a*, 120*b* represent the low threshold values as described referring to FIG. 11. The region surrounded by the dashed line in a scatter diagram 121 shown in FIG. 12B represents the defect detectable region in the case where the low threshold values 120*a*, 120*b* are set for the respective images under the conditions A and B. This region includes a large number of noises. Results including a large number of noises derived from the respective inspection conditions A and B are integrated, and subjected to the determination as shown in FIG. 11. This makes it possible to newly detect the defect in a shaded region 122 of the scatter diagram 121 In FIG. 12B relative to those detected based on the normal threshold value without detecting the noise.

As described above, according to the present invention, two kinds of input images are individually subjected to the defect candidate detection process (8-2) for each inspection condition so that the defect determination is executed by the post-inspection process (8-3) using the defect candidate information detected under the respective conditions. This makes it possible to check the defect by performing simple coordinate alignment with respect to the images under the two inspection conditions, which make the images differently appeared. The image by itself is not required for integration, and accordingly, the high-capacity storage medium is not necessary when obtaining results of the inspection conditions on time-series basis. It is therefore possible to easily integrate the results derived from three or more inspection conditions. In the integration example as described above, the brightness difference between the detected image and the reference image is set as the feature quantity for discrimination between the defect and noise. Plural other features may be used for the determination.

As shown in FIG. 8, according to the present invention, the feature quantity value for each defect is calculated and output through the defect candidate detection process, which may be employed as well. This makes it possible to conduct advanced discrimination between noise and defect, and to expand the new defect detectable region 122 shown in FIG. 12B.

As shown in FIG. 8, according to the present invention, the small region image for each defect is also extracted and output through the defect candidate detection process. This makes it possible to calculate the new feature quantity from the small regional image as well. Those calculated values are integrated to conduct the discrimination between noise and defect. When the small regional images are integrated to subject the defect to determination again, classification, and dimension estimation, there may not be the case where the small regional images are all derived from both the inspection conditions. For example, there may be the defect candidate which is not detected based on the low threshold value under the inspection condition A, but is detected subsequently under the inspection condition B. If the defect candidate is extracted under the inspection condition B and is not detected under the inspection condition A, the inspection condition A is set again so that the image at the position detected under the inspection condition B is obtained again. This makes it possible to provide all the small regional images from both the conditions. The image in the limited region, for example, the region of the defect candidate detected from the inspection condition B may only be obtained, thus reducing the time for obtaining the image again. The defects of the images from both the conditions may be classified based on the ratio between the shading difference of the defect portion calculated under the inspection condition A with respect to the reference image $DA(x,y)=fA(x,y)-gA(x,y)$ and the shading difference of the defect portion calculated under the inspection condition B with respect to the reference image $DB(x,y)=fB(x,y)-gB(x,y)$.

$$R(x,y)=DA(x,y)/DB(x,y)$$

If $R(x,y)>Th$ then foreign substance
else scratch

When the defect type is identified by the classification as represented by the above example, the dimension estimation is performed. Relationship between the amount of scattered light and the dimension varies depending on the defect type. There may be the case where the amount of scattered light of the obtained image is large in spite of a very small foreign substance, and in contrast, the amount of scattered light of the obtained image is small in spite of a large scratch. Dimension estimation is performed after identifying the defect type so as to ensure more accurate estimation. For example, the relationship between the amount of scattered light (feature quantity such as brightness value of the defect portion) and the dimension is preliminarily calculated for each defect type using the optical simulation so as to refer to the data with respect to the relationship between the amount of scattered light and the dimension in accordance with the defect type.

According to the inspection apparatus as described in the embodiments of the present invention, plural images which appear different owing to plural detection conditions and optical conditions are individually input to the image processing unit so as to detect the defect candidates. The obtained defect candidate information data are integrated to make a final determination with respect to defect/non-defect. This makes it possible to realize the defect extraction with high sensitivity. The defect candidates extracted from plural images which appear different may be integrated by checking the position where the defect candidate is generated (coordinate at a generation point) on the wafer. This may simplify the integration. When plural defect candidates under the different conditions are obtained on time-series basis, the high-capacity storage medium is not required, thus allowing the high-speed inspection with high sensitivity, which may be easily conducted.

Although there may be subtle difference in the pattern thickness after planarization process such as CMP, and large luminance deviation between chips to be compared owing to short wavelength of the illuminating light, the present invention allows detection of the defect ranging from 20 nm to 90 nm.

Upon Low-k film inspection of the inorganic insulation film such as $SiO_2$, SiOF, BSG, SiOB, porous ciliary film, and the organic insulation film such as $SiO_2$ that contains methyl group, MSQ, polyimide film, parylene film, Teflon™ film, and amorphous carbon film, the present invention allows detection of the defect ranging from 20 nm to 90 nm in spite of difference in the local luminance owing to dispersion of the refractive index in the film.

An embodiment of the present invention has been described, taking the comparative inspection image with respect to the semiconductor wafer using the dark-field inspection apparatus as the example. However, the present invention is applicable to the comparative image for electron pattern inspection using a SEM, and the pattern inspection apparatus under the bright-field illumination as well.

The inspection subject is not limited to the semiconductor wafer. For example, TFT substrate, photomask, printed circuit board and the like may be subjected to the inspection so long as the defect is detected by making comparison between images.

The present invention easily allows detection of various types of defects with high sensitivity and suppression of noise and Nuisance defect which increase accompanied with the detection with high sensitivity.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

REFERENCE SIGNS LIST 1 optical unit
2 memory
3 image processing unit
4a, 4b lighting units
5 semiconductor wafer
7a, 7b detection units
8-2 defect candidate detection unit
8-3 post-inspection processing unit
31, 32 sensor units
9 overall control unit

The invention claimed is:

1. A defect inspection apparatus comprising:
an illumination optical system configured to irradiate an inspection subject, under a plurality of inspection conditions;
a detection optical system configured to detect scattered light from the inspection subject irradiated by the illumination optical system, under the plurality of inspection conditions, and to obtain a plurality of images under the plurality of inspection conditions; and
an image processing system that includes:
a defect candidate detection unit configured to detect defect candidates with respect to a plurality of images obtained by the detection optical system, under the plurality of inspection conditions, respectively, by using a first threshold and a second threshold lower than the first threshold, and
a post-inspection processing unit configured to execute a defect determination, by differentiating defects from noise, and by integrating features of the defect candidates with respect to the plurality of images obtained under the plurality of inspection conditions,
wherein in the post-inspection processing unit:
a defect candidate detected by the defect candidate detection unit is determined to be a defect when detected in at least one of the plurality of images obtained by the detection optical system, under the plurality of inspection conditions, by applying the first threshold, or alternatively, the defect is detected in all of the plurality of images obtained by the detection optical system, under the plurality of inspection conditions, by applying the second threshold, and
a defect candidate is determined to be noise when the defect candidate is detected in less than all of the plurality of images obtained by the detection optical system, under the plurality of inspection conditions, by applying the second threshold.

2. The defect inspection apparatus according to claim 1, wherein the post-inspection processing unit is configured to execute the defect determination, by integrating the defect candidates, by checking coordinates of the defect candidates with respect to the plurality of images under the plurality of inspection conditions.

3. The defect inspection apparatus according to claim 1, wherein the post-inspection processing unit is configured to check the coordinates of the defect candidates with respect to the plurality of images under the plurality of inspection conditions, and to determine whether or not the defect candidates are observed through detection with respect to all the plurality of images under the plurality of inspection conditions.

4. The defect inspection apparatus according to claim 1, wherein the post-inspection processing unit is configured to classify a defect according to type, based on the plurality of images, and further to execute a dimension estimation of the classified defect.

5. A defect inspection method comprising:
an illumination step of irradiating a surface of an inspection subject, under a plurality of inspection conditions;
a detection step of obtaining a plurality of images, by detecting scattered light from the surface of the inspection subject irradiated in the illumination step under the plurality of inspection conditions;
a defect candidate detection step of detecting defect candidates, with respect to the plurality of images detected in the detection step under the plurality of inspection conditions, by using a first threshold and a second threshold lower than the first threshold; and
a post-inspection processing step of executing a defect determination, by differentiating defects from noise, by checking coordinates of the defect candidates detected with respect to the plurality of inspection conditions, and by integrating features of the defect candidates with checked coordinates with respect to the plurality of images obtained under the plurality of inspection conditions,
wherein in the post-inspection processing step:
a defect candidate detected at the defect candidate detection step is determined to be a defect when detected in at least one of the plurality of images obtained at the detection step under the plurality of inspection conditions, by applying the first threshold, or alternatively, the defect is detected in all of the plurality of images obtained at the detection step under the plurality of inspection conditions, by applying the second threshold, and
a defect candidate is determined to be noise when the defect candidate is detected in less than all of the plurality of images obtained at the detection step under the plurality of inspection conditions, by applying the second threshold.

6. The defect inspection method according to claim 5, wherein the post-inspection processing step executes the defect determination by integrating the defect candidates, by checking coordinates of the defect candidates with respect to the plurality of images obtained under the plurality of inspection conditions.

7. The defect inspection method according to claim 5, wherein the post-inspection processing step checks the coordinates of the defect candidates with respect to the plurality of images obtained under the plurality of inspection conditions, and determines whether or not the defect candidates are obtained through detection with respect to all the plurality of images obtained under the plurality of inspection conditions.

8. The defect inspection method according to claim 5, wherein the post-inspection processing step includes a sub-step of classifying a defect according to type based on the plurality of images, and further includes a sub-step of executing a dimension estimation with respect to the classified defect.

* * * * *